(12) United States Patent
Geiger et al.

(10) Patent No.: US 8,945,082 B2
(45) Date of Patent: Feb. 3, 2015

(54) TUBE WITH A FEMALE LUER LOCK FITTING

(75) Inventors: Andreas Geiger, Steffisburg (CH);
Christian Kubesch, Oberdiessbach (CH); Mario Schüpbach, Konolfingen (CH)

(73) Assignee: Hoffman Neopac AG (CH)

( * ) Notice: Subject to any disclaimer, the term of this patent is extended or adjusted under 35 U.S.C. 154(b) by 0 days.

(21) Appl. No.: 13/820,566

(22) PCT Filed: Dec. 14, 2010

(86) PCT No.: PCT/CH2010/000312
§ 371 (c)(1),
(2), (4) Date: Mar. 4, 2013

(87) PCT Pub. No.: WO2012/079180
PCT Pub. Date: Jun. 21, 2012

(65) Prior Publication Data
US 2013/0165851 A1    Jun. 27, 2013

(51) Int. Cl.
*A61B 19/00* (2006.01)
*A61J 1/06* (2006.01)
*A61M 5/50* (2006.01)
*A61J 1/20* (2006.01)

(52) U.S. Cl.
CPC .............. *A61J 1/067* (2013.01); *A61M 5/5086* (2013.01); *A61J 1/2089* (2013.01); *A61J 2001/2027* (2013.01)
USPC ............................ 604/403; 604/411; 604/415

(58) Field of Classification Search
USPC .................................................. 604/403–416
See application file for complete search history.

(56) References Cited

U.S. PATENT DOCUMENTS

| 5,924,584 A * | 7/1999 | Hellstrom et al. ............ 215/247 |
| 6,692,478 B1 | 2/2004 | Paradis |
| 2013/0123713 A1* | 5/2013 | Utterberg et al. ............ 604/244 |

FOREIGN PATENT DOCUMENTS

| DE | 295 02 544 | 6/1996 |
| WO | WO 02/053086 A1 | 7/2002 |
| WO | WO 2008/036889 A2 | 3/2008 |

OTHER PUBLICATIONS

International Search Report dated Aug. 16, 2011 issued in corresponding international patent application No. PCT/CH2010/000312.

* cited by examiner

*Primary Examiner* — Philip R Wiest
*Assistant Examiner* — Benjamin Klein
(74) *Attorney, Agent, or Firm* — Ostrolenk Faber LLP

(57) ABSTRACT

The disclosure relates to tube with a tube head (4) and a container (5) made of resilient material, wherein the tube head (4) is connected to the container (5), wherein the tube head (4) comprises a female Luer lock fitting (7) with a flow passage (17), the female Luer lock fitting (7) being designed for sealingly receiving a male Luer lock fitting (9) of a syringe (2), wherein a tamper-evident closure (11, 12, 13, 14) is arranged at the inner surface of the female Luer lock fitting (7) such that it closes the flow passage (17) in a closed state of the tube (1).

3 Claims, 3 Drawing Sheets

TUBE WITH A FEMALE LUER LOCK FITTING

CROSS REFERENCE TO RELATED APPLICATIONS

The present application is a 35 U.S.C. §371 National Phase conversion of PCT/CH2010/000312, filed Dec. 14, 2010, the disclosure of which is incorporated herein by reference. The PCT International Application was published in the English language.

TECHNICAL FIELD

The invention relates to a tube with a tube head and a container according to the preamble of claim 1.

BACKGROUND OF THE INVENTION

Liquid pharmaceutical products for parenteral use e.g. through injection or infusion are often stored in glass vials with a stopper or in glass ampoules. In order to gain access to the stored pharmaceutical products typically several handling steps are necessary. Furthermore, hypodermic needles are required for extracting the pharmaceutical product.

If, for example, a pharmaceutical product shall be extracted from a glass ampoule, the pharmaceutical product has first to be transferred from the ampoule head back into the ampoule body before removal of the ampoule head for opening of the glass ampoule. Then the ampoule head has to be removed from the ampoule body either by sawing off the ampoule head by applying two to three sawing strokes with an ampoule saw to a predetermined breaking point at the ampoule neck, the ampoule shoulder connecting the ampoule head with the ampoule body. The predetermined breaking point is typically identified by a coloured point at or coloured ring around the ampoule neck. In case the glass ampoule is a break ampoule, the ampoule is opened by hand in that a non-sterile swab is held with the index finger behind the ampoule neck to avoid cuts and the ampoule head is then broken away with the thumb as lever. After the glass ampoule has been opened the liquid pharmaceutical product is completely extracted from it and transferred to a syringe by means of a first hypodermic needle. After that the first hypodermic needle is disposed, as it might be contaminated, and possible air is removed from the syringe by moving air bubbles to its orifice through tapping on the syringe body. After the removal of possible air a sterile second hypodermic needle is placed on the syringe for administering of the pharmaceutical product to a patient through injection. The first hypodermic needle is not used for n the injection as it might have been contaminated through exposure to unsterile air. Instead a sterile second hypodermic needle is used for injection, which makes handling rather involved and time-consuming.

During opening of a break ampoule glass splinters may be formed that might enter the pharmaceutical product and that thus might be injected a patient during administration of the extracted pharmaceutical product.

If the pharmaceutical product is stored in a glass vial with a rubber stopper placed across and partly inside its neck, first a metal or plastic closure of the glass vial has to be removed. Then the rubber stopper has to be disinfected, with the disinfecting agent being typically applied for a predetermined amount of time. For extracting the pharmaceutical product a syringe with a hypodermic needle as be used, wherein unsterile ambient air is first sucked into the syringe through the hypodermic needle and than injected into the vial when piercing the hypodermic needle through the rubber stopper to create a positive pressure inside the vial. This has, however, the disadvantage that the pharmaceutical product might be contaminated by the unsterile air. Without the creation of the positive pressure inside the vial, the pharmaceutical product is hard to extract as the glass vial is not resilient.

To avoid the introduction of unsterile ambient air into the glass vial an adapter in form of a so-called mini-spike in conjunction with a hypodermic needle or a special hypodermic needle with integrated ventilation with filter may be used. A mini-spike is a plastic part with a hollow plastic spike by means of which the rubber stopper can be penetrated to extract the pharmaceutical product through the hypodermic needle placed in-side the hollow plastic spike. Excess pharmaceutical product that has been extracted is disposed of. Partly emptied glass vials are labelled with date and time as they may be used for 24 hours after opening. When piercing the rubber stopper with a hypodermic needle or a mini-spike for extraction of the pharmaceutical product, rubber particles are, however, potentially formed depending on the type and size of the used needle/spike that might contaminate the pharmaceutical product and that might then be injected a patient.

SUMMARY OF THE INVENTION

It is an object of the invention to provide a tube for a pharmaceutical product that is to be applied parenterally, which allows for relatively easy and fast extraction of the pharmaceutical product with decreased risk of contaminating the pharmaceutical product. It is a further object of the invention to provide a tube for a pharmaceutical product, from which a pharmaceutical product can be extracted without the use of a hypodermic needle.

In order to implement these and still further objects of the invention, which will become more readily apparent as the description proceeds, a tube with a tube head and a container is provided. The container is made of resilient material and is aimed for containing the pharmaceutical product. The tube head comprises a female Luer Lock fitting that is designed for sealingly, i.e. in an air-tight manner, receiving a male Luer lock fitting of a syringe, in particular a syringe without a needle, wherein the male Luer lock fitting of the syringe can be screwed on the female Luer lock fitting of the tube of the invention, with threads in an inner sleeve of the male Luer lock fitting engaging with a hub of the female Luer lock fitting. The female Luer lock fitting is provided with a flow passage at its inside that connects with the interior of the container of the tube. At the inner surface of the female Luer lock fitting is sealingly, i.e. air-tightly, arranged a tamper-evident closure that closes the flow passage of the female Luer lock fitting in a closed state of the tube.

The tamper-evident closure is designed such that it opens, thereby unblocking the flow passage, when a needle-less syringe with a male Luer lock fitting is screwed onto the female Luer lock fitting of the tube according to the invention sufficiently far to exert pressure/force on the tamper-evident closure.

The tamper-evident closure preferably comprises a lid that is sealingly arranged at and connected with the inner surface of the female Luer lock fitting such that it completely closes the flow passage in the closed state of the tube. The lid is connected to the inner surface of the female Luer lock fitting through a hinge, i.e. the hinge connects the inner surface of the female Luer lock fitting with the lid. The lid is further connected with the inner surface of the female Luer lock fitting through a predetermined breaking line that connects to the hinge, such that the lid is all around connected to the inner surface of the female Luer lock fitting. The hinge and the predetermined breaking line form part of the tamper-evident closure. Thus, in a closed state of the tube the lid is sealingly and air-tightly connected to the inner surface of the female Luer lock fitting by means of the hinge and the predetermined breaking line.

If a needle-less syringe is screwed sufficiently far onto the female Luer lock fitting of the tube of the invention, the tamper-evident closure is opened through the pressure/force that the syringe exerts on it, in that the predetermined breaking line is broken and—moved by the inserted syringe—the lid rotates around the axis of rotation of the hinge downwards and sideways, thereby unblocking the flow passage in the female Luer lock fitting, such that the pharmaceutical product can be sucked from the container into the syringe by the syringe. The expression 'downwards' is defined as the direction towards the container of the tube. The expression 'sideways' is defined as a direction laterally away from a longitudinal centre axis of the tube.

In the inner surface of the female Luer lock fitting of the tube of the invention preferably a receiving space is provided for receiving the lid, when the tamper-evident closure has been opened, i.e. the predetermined breaking line has been broken and the lid has been moved by the inserted syringe such that the lid has been rotated around the axis of rotation of the hinge. It can thus be avoided that the lid is ripped entirely off the inner surface of the female Luer lock fitting and thereby possibly blocks the flow passage completely or partly. The dimensions of the receiving space are preferentially such that the lid once completely received from the receiving space does not project into the flow passage of the female Luer lock fitting, so that the flow of the pharmaceutical product through the flow passage is not hampered by the lid.

After the tamper-evident closure has been opened, in particular in that the predetermined breaking line has been broken and the lid has been moved into the receiving space, the pharmaceutical product can be extracted from the tube by means of the syringe. As the material of the tube is resilient, the resilience of the tube compensates for the negative pressure that arises during the extraction of the pharmaceutical product. The turning off of the pharmaceutical product takes place at the tube of the invention by screwing off the filled syringe. For administration of the pharmaceutical product to a patient a hypodermic needle is placed on the male Luer lock fitting of the syringe.

The tube of the invention is of resilient material. Furthermore, the material of the tube or at least of its container is preferably transparent such that a user can see how much of the pharmaceutical product is left inside the tube. The material of the tube may, for example, be a preferably transparent mono material such as polyethylene (PE), polypropylene (PP) or similar. The material of the tube or at least its container may also be a barrier laminate. Such a barrier laminate can comprise films that are coated for use as barrier layers and/or films that consist of barrier material such as cyclic olefin copolymer (COC), polychlorotrifluoroethylene (PCTFE), ethylene vinyl alcohol (EVOH) or similar.

With the tube according to the invention advantageously no additional hypodermic needle is needed for extraction of the pharmaceutical product from the tube, i.e. there is no need for a needle change from a needle for extraction to a needle for administration of the pharmaceutical product for reasons of avoiding contamination. Just one hypodermic needle is needed, namely for the administration of the pharmaceutical product to the patient from the syringe. There is no need to change hypodermic needles in the present invention as a needle-less syringe can be placed sealingly, i.e. air-tightly, directly on the tube of the invention. Also no adapter or additional means such as a mini-spike is required for securely transferring the pharmaceutical product to the syringe as the needle-less syringe can be placed directly and sealingly on the tube. Furthermore, no unsterile air must be injected into the tube to generate a positive pressure for extraction of the pharmaceutical product from it. As the tube comes without a stopper, there is no rubber stopper that requires disinfection before use of the tube and rubber particles contaminating the pharmaceutical product can be avoided. Further, as the tube comprises no glass parts that need to be broken for extraction of the pharmaceutical product, contamination of the pharmaceutical product with glass particles is thus not an issue.

Extracting the pharmaceutical product from the tube of the invention with a syringe with a male Luer lock fitting is simple and fast. Due to the tight fit between the female Luer lock fitting of the tube of the invention and a male Luer lock fitting of a syringe the influence of human errors, in particular with respect to possible contamination of the pharmaceutical product, can advantageously be reduced or even minimized.

Furthermore, the user of the tube of the invention is protected from coming into contact with a possible toxic pharmaceutical product, when transferring the toxic pharmaceutical product from the tube of the invention to the syringe. Toxic pharmaceutical products are often used in oncological treatments.

The tube according to the invention can be used in particular for containing pharmaceutical products for parenteral injection, replacing the typically nowadays employed glass ampoules and glass vials with stopper.

The invention further relates to a system comprising a needle-less syringe with a male Luer lock fitting and an inner sleeve and with a tube of the invention, wherein the female Luer lock fitting of the tube is designed such that the male Luer lock fitting of the syringe sealingly fits into the female Luer lock fitting of the tube and wherein the tamper-evident closure of the tube opens when pressure/force is exerted on the tamper-evident closure by the inner sleeve of the syringe when the male Luer lock fitting of the syringe is screwed sufficiently head of the tube.

BRIEF DESCRIPTION OF THE DRAWINGS

Further advantageous features and applications of the invention can be found in the depending claims as well as in the following description of the drawings illustrating the invention. In the drawings like reference signs designate the same or similar parts throughout the several figures of which:

DESCRIPTION OF PREFERRED EMBODIMENTS

Figure 1:
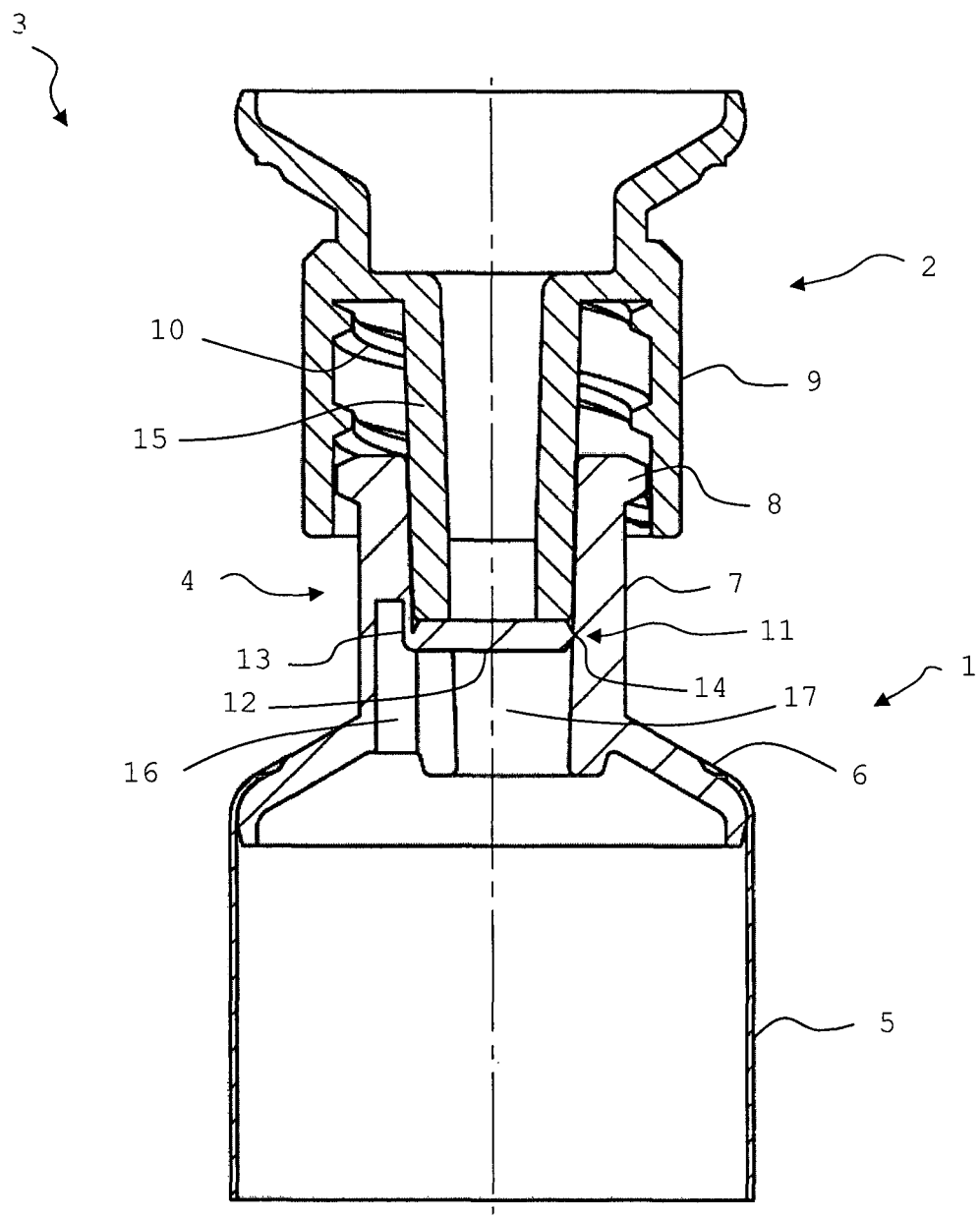
FIG. 1 depicts a sectional view of a tube of the invention with a needle-less syringe inserted into the tube.
Figure 2:
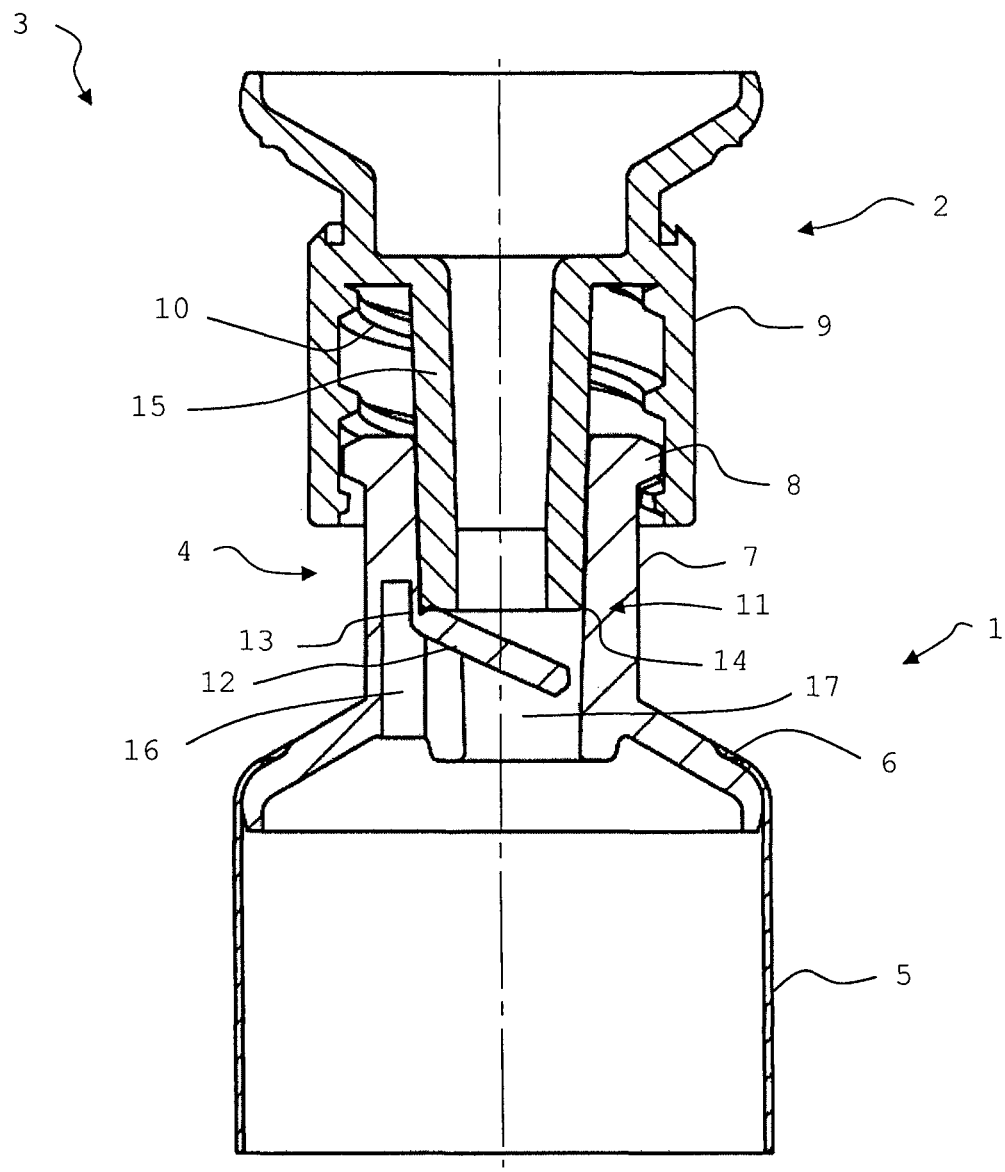
FIG. 2 depicts a sectional view of the tube of the invention shown in FIG. 1 with the needle-less syringe being further inserted into the tube.
Figure 3:
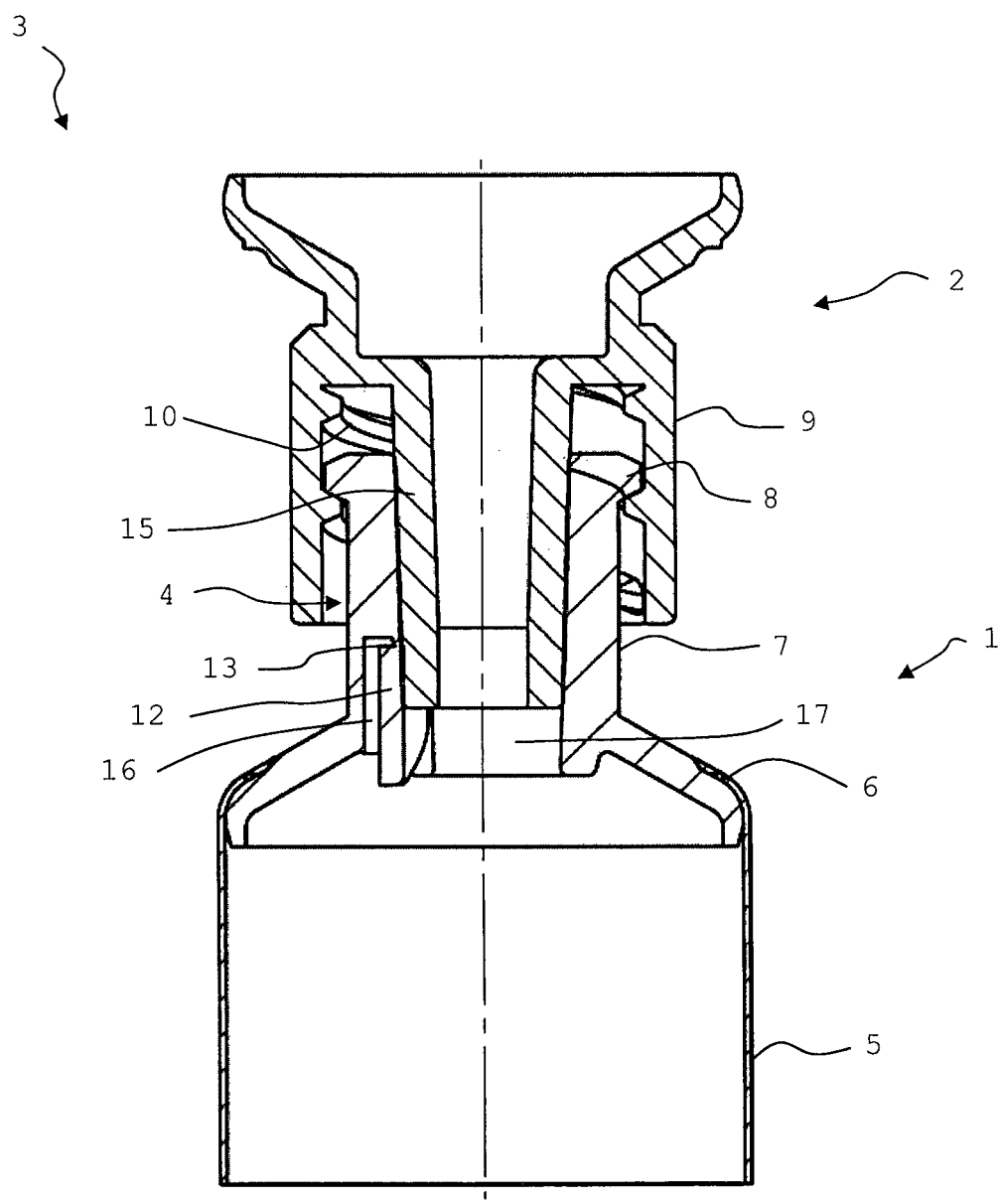
FIG. 3 depicts a sectional view of the tube of the invention shown in FIGS. 1 and 2 with the needle-less syringe being still further inserted into the tube.

FIGS. 1 to 3 depict a tube 1 according to the invention with a needle-less syringe 2 introduced into it, i.e. FIGS. 1 to 3 depict also a system 3 according to the invention comprising the tube 1 and the syringe 2.

The tube 1 comprises a tube head 4 and a container 5, with the upper part of the container 5 depicted, the container 5 being connected to the tube head 4 by way of a shoulder 6. The container 5 is aimed for holding a liquid pharmaceutical product (not shown). The tube 4 of the tube 1 comprises a female Luer lock fitting 7 with a hub 8. The syringe 2 comprises a male Luer lock fitting 9 with threads 10. When the syringe 2 is introduced into the tube head 4 by screwing it onto the tube head 4, the threads 10 of its male Luer lock fitting 9 engage with the hub 8 of the female Luer lock fitting 7 of the tube head 4. The outer surface of the inner sleeve 15 of the male Luer lock fitting 9 of the syringe 2 engages sealingly and thus air-tightly with the inner surface of the female Luer lock fitting 7 of the tube head 4. On the inner surface of the female Luer lock fitting 7 of the tube head 4 there is provided a tamper-evident closure 11 that comprises a lid 12, a hinge 13 and a predetermined breaking line 14.

FIG. 1 depicts the tube 1 in a closed state, i.e. the tamper-evident closure 11 sealingly and thus air-tightly closes the flow passage 14 of the female Luer lock fitting 7 of the tube head 4, i.e. the lid 12 is sealingly connected with the inner surface of the female Luer lock fitting 7 by means of the hinge 13 and the (unbroken) predetermined breaking line 14. The lid 12 is all around connected to the inner surface of the female Luer lock fitting 7 by means of the hinge 13 and the (unbroken) predetermined breaking line 14 with the predetermined breaking line 14 being connected to the hinge 13 at both of its ends. In FIG. 1 the syringe 2 has been screwed onto the tube head 4 by engaging the threads 10 of the male Luer lock fitting 9 of the syringe 2 with the hub 8 of the female Luer lock fitting 7 of the tube head 4. However, the syringe 2 has not been screwed that far onto the tube head 4 that it exerts enough pressure/force onto the lid 12 of the tamper-evident closure 11 that the predetermined breaking line 14 breaks.

FIG. 2 depicts the tube 1 and the syringe 2 of FIG. 1, but with the syringe 2 being further screwed onto the tube head 4 of the tube 1. The inner sleeve 15 of the male Luer lock fitting 9 of the syringe 2 now exerts enough pressure/force onto the tamper-evident closure 11 that it opens such that the flow passage 17 is not longer fully blocked. In particular, the inner sleeve 15 of the male Luer lock fitting 9 of the syringe 2 exerts enough pressure/force onto the lid 12 that the predetermined breaking line 14 breaks and the lid 12 is now only connected to the inner surface of the female Luer lock fitting 7 of the tube head 4 by way of the hinge 13, with the lid 12 having been rotated by the inner sleeve 15 of the syringe 2 by an acute angle around the rotation axis of the hinge 13.

FIG. 3 depicts the tube 1 and the syringe 2 of FIGS. 1 and 2 with the syringe 2 being even further screwed onto the tube head 4 such that the inner sleeve 15 of the syringe 2 moves even deeper into the tube head 4, such that the tamper-evident closure 11 opens even more, in that the lid 12 is rotated even more around the axis of rotation of the hinge 13. FIG. 3 depicts an open state of the tube 1, wherein the flow passage 17 of the female Luer lock fitting 7 of the tube head 4 is completely unblocked as the lid 12 has been rotated by around 90 degrees around the axis of rotation of the hinge 13 and has been completely received by a receiving space 16 for the lid. The receiving space 16 is located sufficiently deep inside the inner surface of the female Luer lock fitting 7 of the tube head 4 that it can receive the entire lid 13, i.e. the dimensions of the receiving space 16 correspond to the outer dimensions of the lid 13, such that the lid 13 that is completely received by the receiving space does not project into the flow passage 17. The receiving space 16 is open towards the flow channel 14 for receiving the lid 13.

Hence the lid 13 can be completely moved into the receiving space 16 by the inner sleeve 15 of the syringe 2, such that the lid 13 is completely moved out of the flow passage 17 of the female Luer lock fitting 7 of the tube head 4 to allow for unblocked flow of the pharmaceutical product from the container 5 throw the flow passage 17 into the syringe 2.

As the tube 1 or at least its container 5 consist of resilient material, negative pressure arising through the suction of the pharmaceutical product into the syringe is advantageously compensated for.

After sufficient pharmaceutical product has been sucked into the syringe 2 it is removed from the tube 4 by unscrewing the male Luer lock fitting 9 of the syringe 2 from the female Luer lock fitting 7 of the tube head 4 of the tube 1.

It is to be understood that while certain embodiments of the present invention have been illustrated and described herein, it is not to be limited to the specific embodiments described and shown.

What is claimed is:

1. A tube comprising:
   a tube head, a container made of resilient material and a shoulder connecting the tube head with the container, the tube head, the container at the shoulder formed integrally,
   wherein the tube head comprises:
   a female Luer lock fitting with a flow passage, the female Luer lock fitting sealingly receiving a male Luer lock fitting of a syringe; and
   a tamper-evident closure arranged at the inner surface of the female Luer lock fitting such that the tamper-evident closure closes the flow passage in a closed state of the tube,
   wherein the tamper-evident closure comprises a lid that is sealingly arranged at the inner surface of the female Luer lock fitting in a closed state of the tube such that the tamper-evident closure closes the flow passage, with the lid being connected to the inner surface of the female Luer lock fitting through a hinge and a predetermined breaking line that connects to the hinge,
   wherein a receiving space is provided in the inner surface of the female Luer lock fitting for receiving the lid in an open state of the tube, and the receiving space is sized and configured such that the lid, once entirely received from the receiving space, does not project into the flow passage of the female Luer lock fitting of the tube head.

2. The tube according to claim 1, wherein the material of the tube is a mono material or a barrier laminate.

3. A system comprising a needle-less syringe with a male Luer lock fitting and an inner sleeve, comprising a tube according to claim 1, wherein the female Luer lock fitting of the tube is configured such that the male Luer lock fitting of the syringe sealingly fits into the female Luer lock fitting of the tube, and
   wherein the tamper-evident closure of the tube opens when pressure is exerted onto the tamper-evident closure by the Inner sleeve of the syringe when the male Luer lock fitting of the syringe is screwed far enough onto the female Luer lock fitting of the tube head of the tube.

* * * * *